United States Patent
Douglas

(10) Patent No.: US 11,210,867 B1
(45) Date of Patent: Dec. 28, 2021

(54) METHOD AND APPARATUS OF CREATING A COMPUTER-GENERATED PATIENT SPECIFIC IMAGE

(71) Applicant: Robert Edwin Douglas, Winter Park, FL (US)

(72) Inventor: Robert Edwin Douglas, Winter Park, FL (US)

( * ) Notice: Subject to any disclaimer, the term of this patent is extended or adjusted under 35 U.S.C. 154(b) by 0 days.

(21) Appl. No.: 16/867,102

(22) Filed: May 5, 2020

Related U.S. Application Data

(63) Continuation of application No. 16/010,925, filed on Jun. 18, 2018, now Pat. No. 10,864,043.

(51) Int. Cl.
*G06T 19/20* (2011.01)
*A61B 34/10* (2016.01)

(52) U.S. Cl.
CPC ........ *G06T 19/20* (2013.01); *A61B 2034/104* (2016.02); *A61B 2034/105* (2016.02); *G06T 2219/004* (2013.01); *G06T 2219/2021* (2013.01)

(58) Field of Classification Search
None
See application file for complete search history.

(56) References Cited

U.S. PATENT DOCUMENTS

| | | | |
|---|---|---|---|
| 2003/0016850 A1* | 1/2003 | Kaufman | G16H 40/63 382/128 |
| 2008/0144901 A1* | 6/2008 | Gering | G06T 15/02 382/130 |
| 2015/0227679 A1* | 8/2015 | Kamer | A61B 34/10 703/11 |
| 2017/0076046 A1* | 3/2017 | Barnes | G16H 40/20 |
| 2017/0367771 A1* | 12/2017 | Tako | A61B 34/20 |

* cited by examiner

*Primary Examiner* — Yanna Wu

(57) ABSTRACT

This patent discloses a method of creating a computer-generated patient specific image to help improve communication amongst health care workers and in between health care workers and patients. Medical data including images, and terminology from a multiple sources is inputted and a computer generated patient specific image is created and optimized for physician-to-physician or physician-to-patient communication.

20 Claims, 20 Drawing Sheets

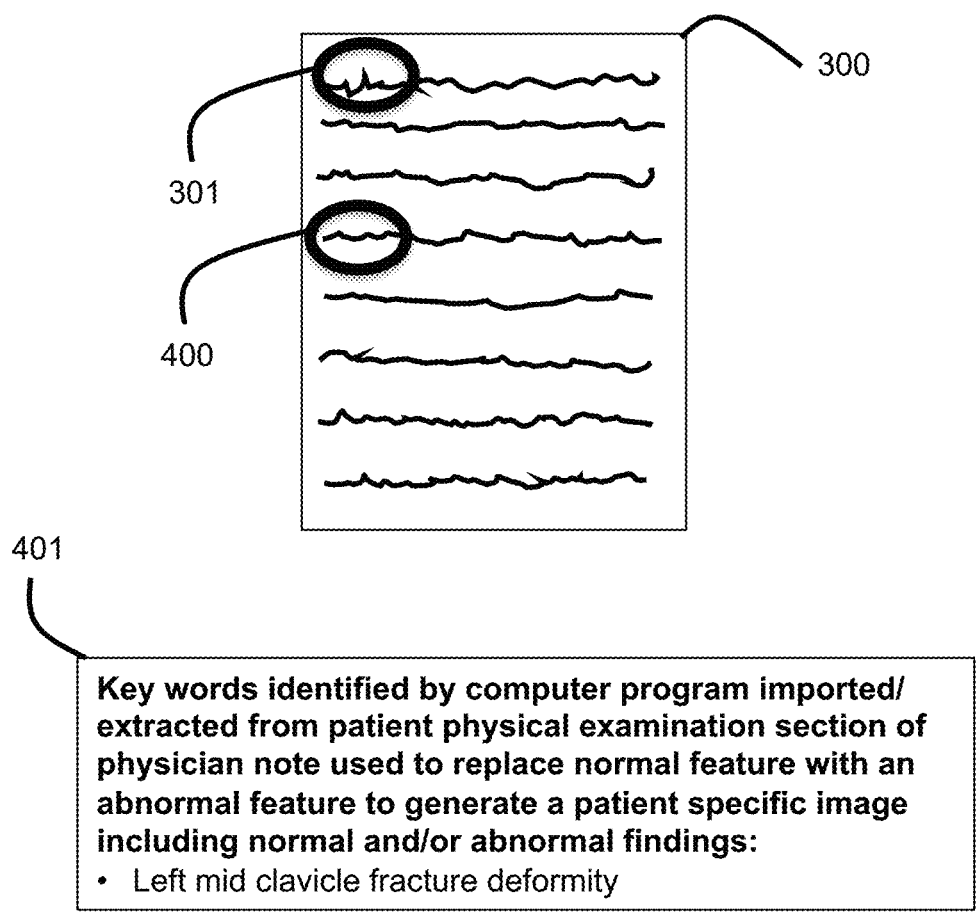
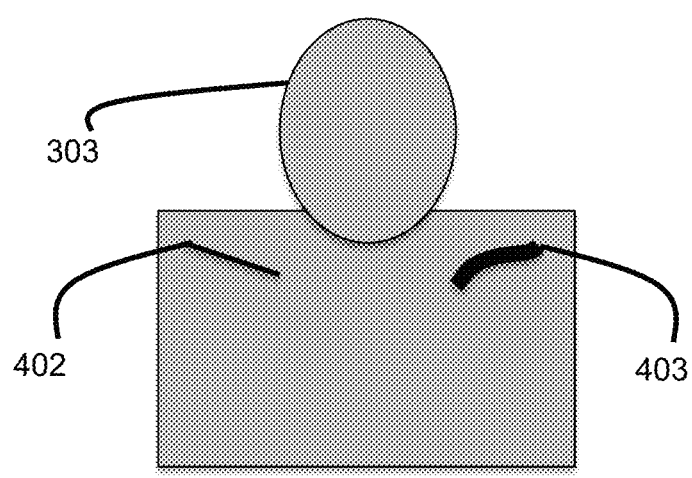
Figure 4

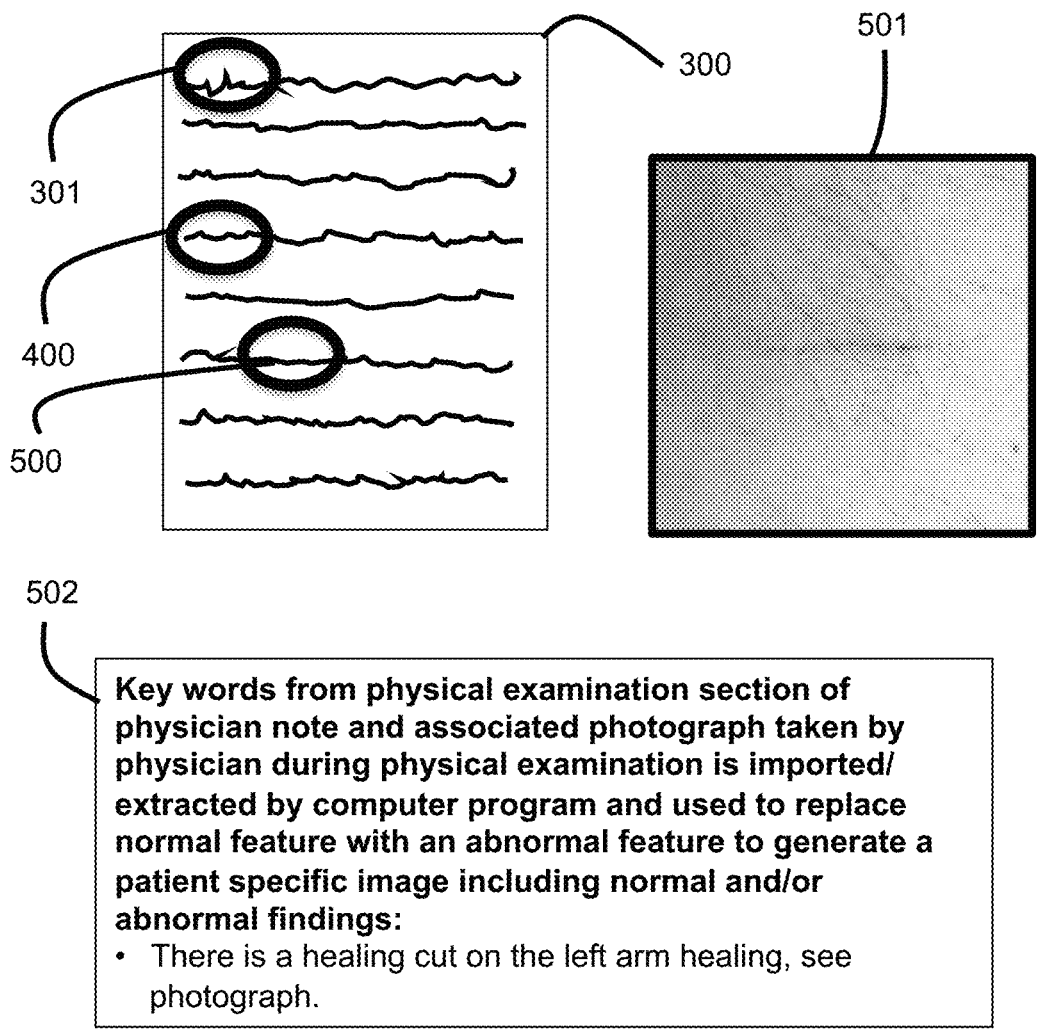

Key words from physical examination section of physician note and associated photograph taken by physician during physical examination is imported/extracted by computer program and used to replace normal feature with an abnormal feature to generate a patient specific image including normal and/or abnormal findings:
- There is a healing cut on the left arm healing, see photograph.

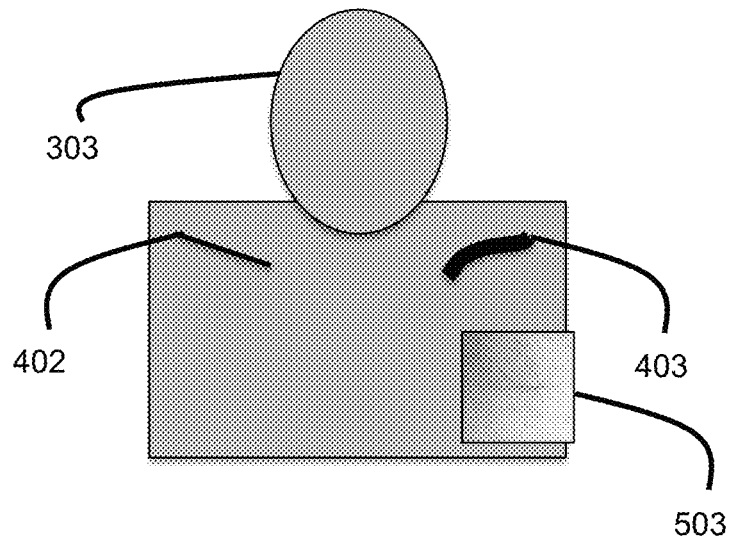

Figure 5

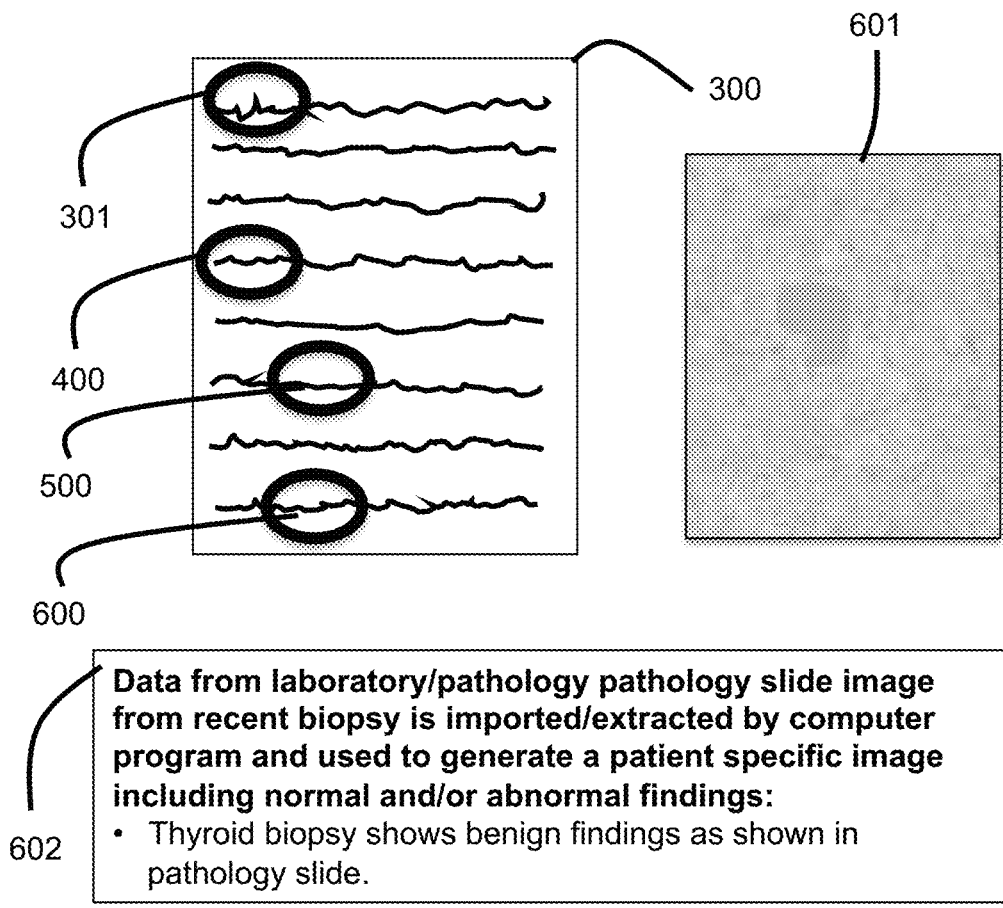
Data from laboratory/pathology pathology slide image from recent biopsy is imported/extracted by computer program and used to generate a patient specific image including normal and/or abnormal findings:
- Thyroid biopsy shows benign findings as shown in pathology slide.
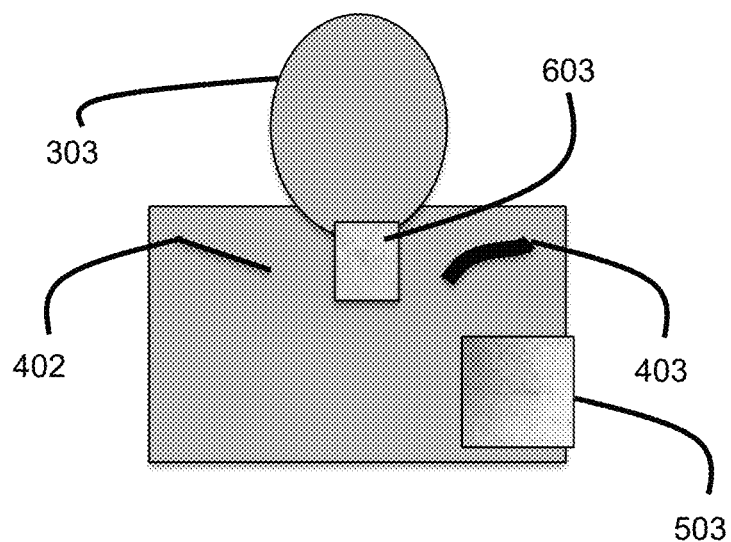
Figure 6

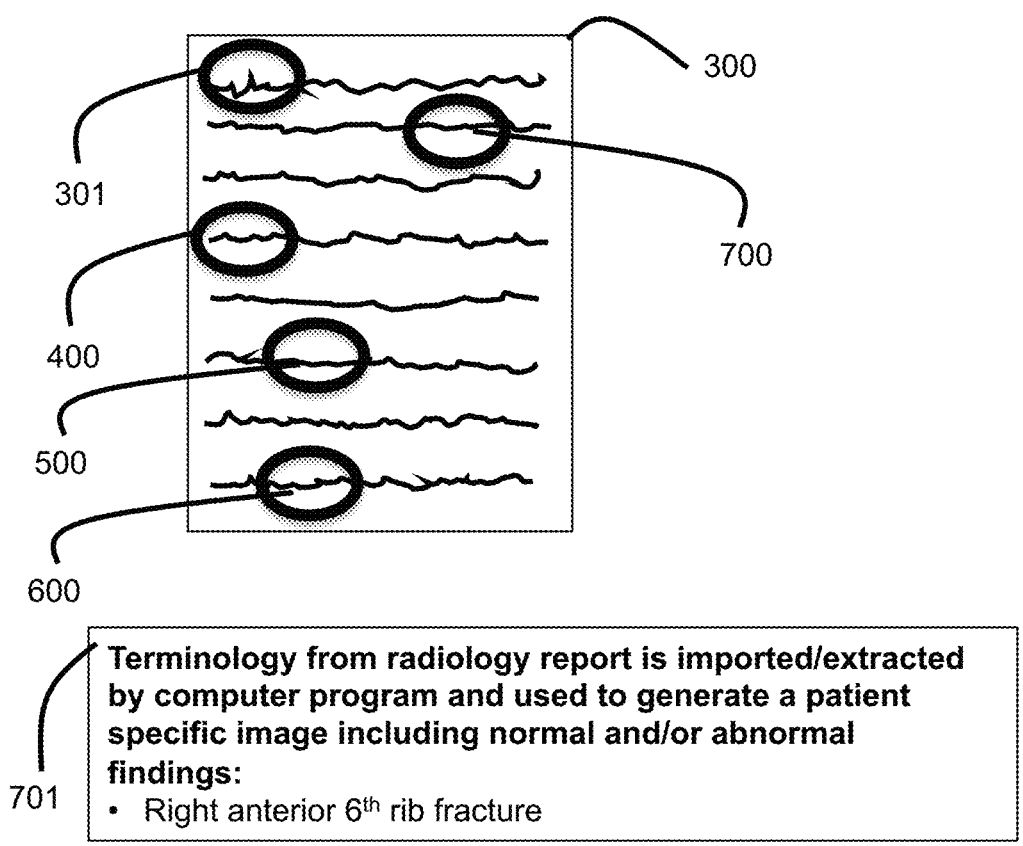
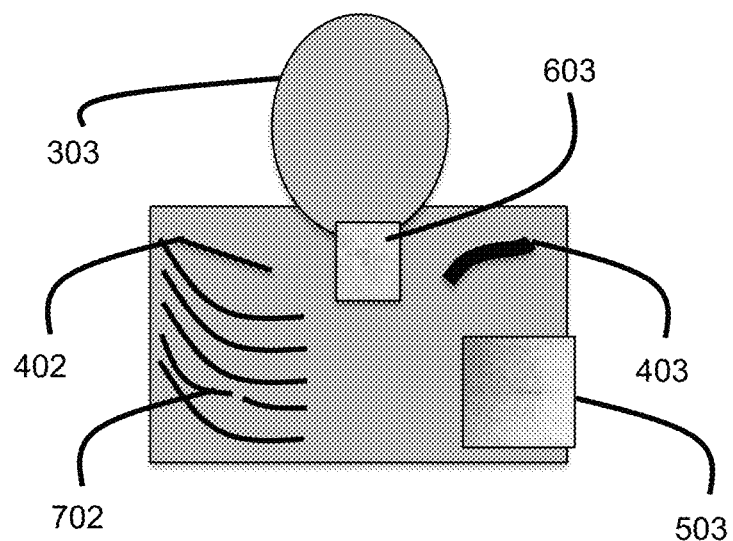
Figure 7

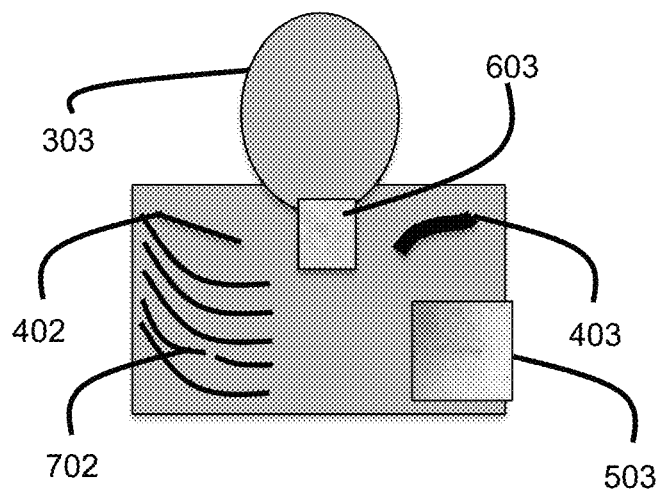
Fig. 9B
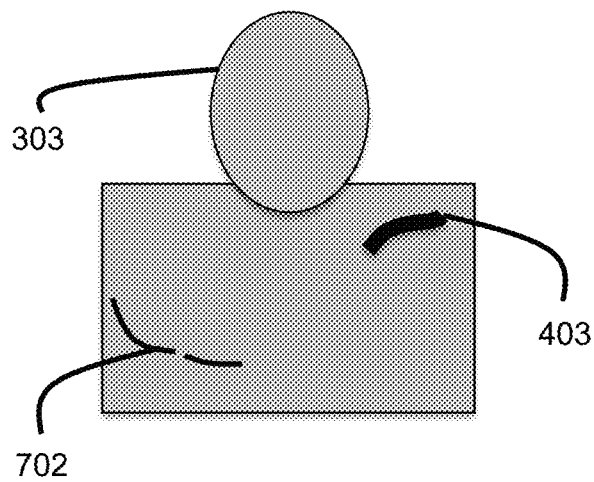
Fig. 9C
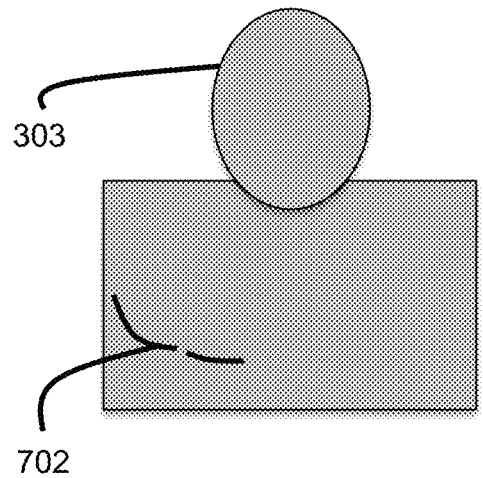

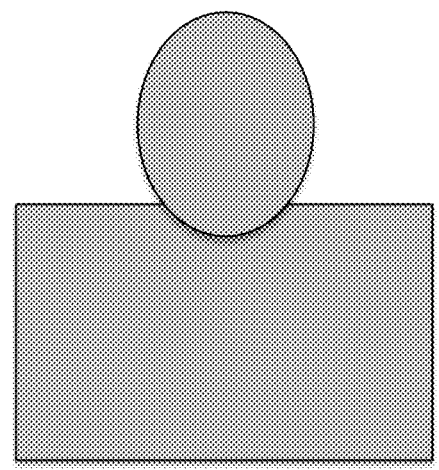
Fig. 12B
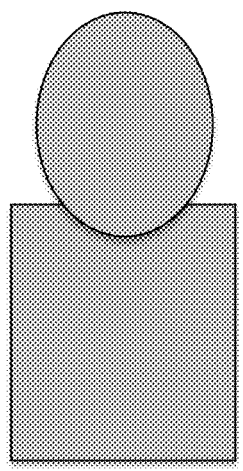
Fig. 12C
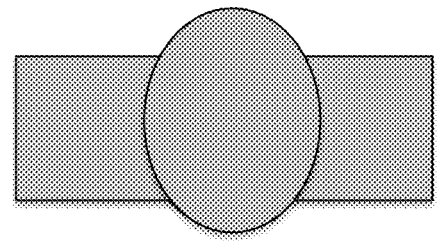

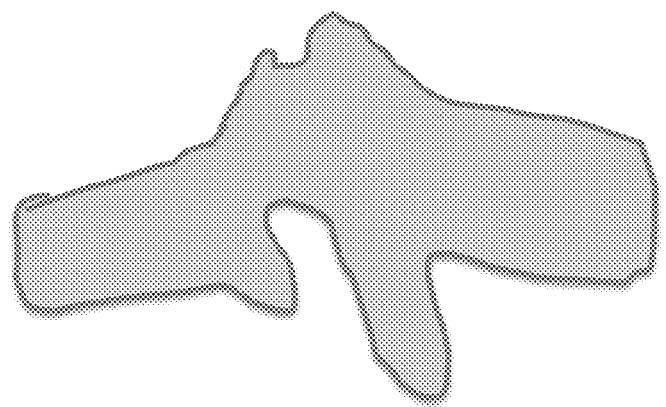
Fig. 13B
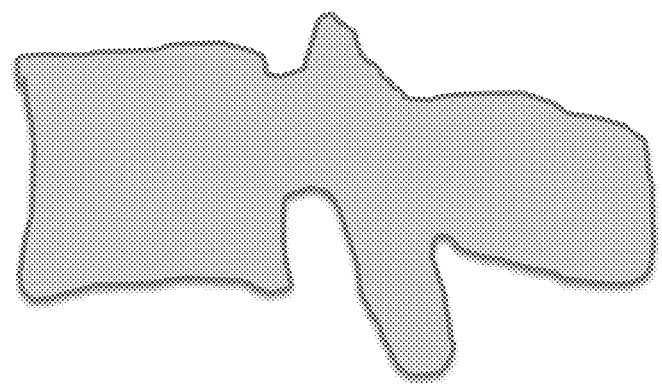

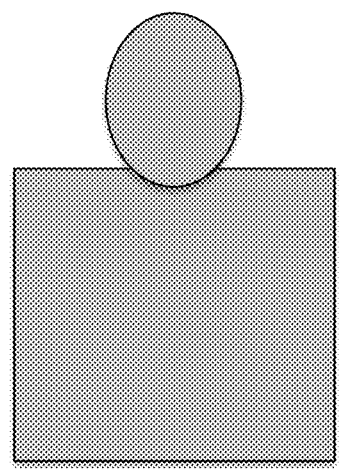
Fig. 14B
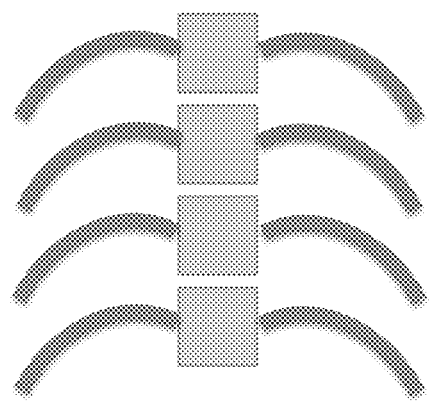

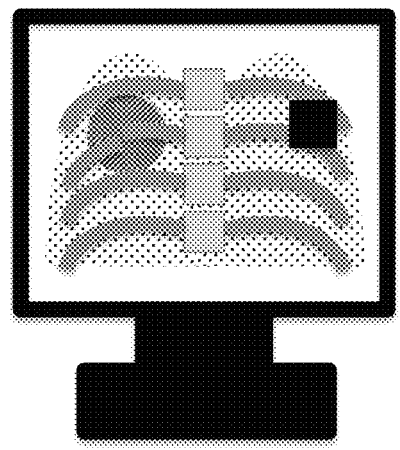
Fig. 16B
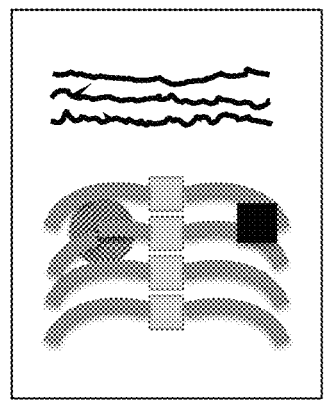
Fig. 16C
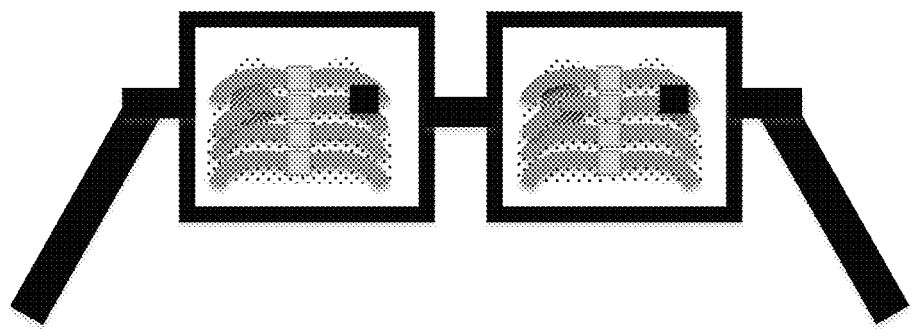

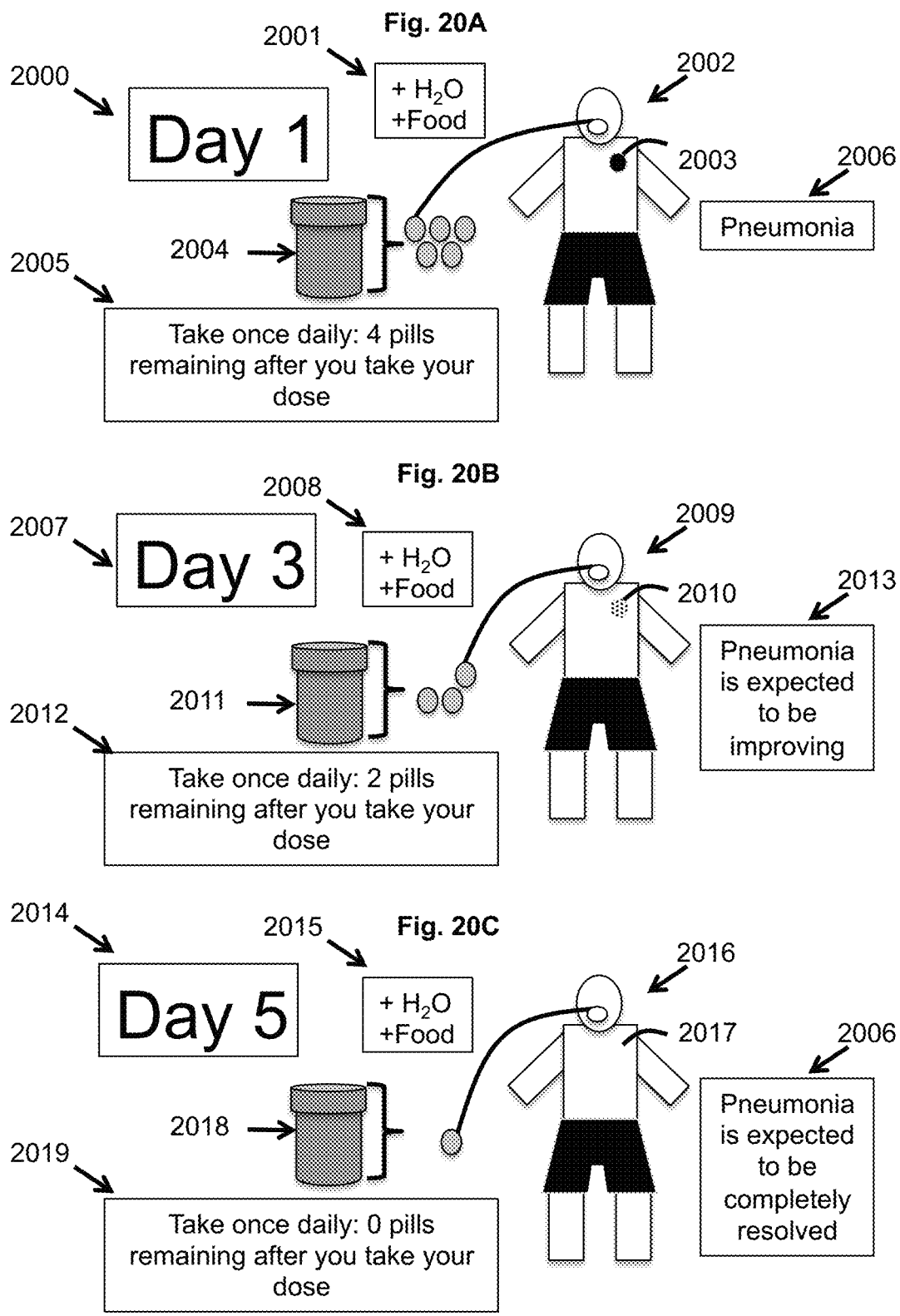

METHOD AND APPARATUS OF CREATING A COMPUTER-GENERATED PATIENT SPECIFIC IMAGE

TECHNICAL FIELD

Aspects of this disclosure are generally related to use of machine, and more particularly machine learning in the medical field.

INTRODUCTION

In the medical system, there are commonly poor medical outcomes due to errors in communication. These communication errors may be between physician and physician or between physician and nurse or between physician and patient.

SUMMARY

All examples, aspects and features mentioned in this document can be combined in any technically conceivable way.

In accordance with an aspect a method comprises: creating a computer-generated patient specific image comprising the inputting of medical data, performing computer processing and outputting a computer-generated patient specific image. In the preferred embodiment, an artificial intelligence program will be utilized, as described in PCT/US2019/023968 Radiologist-assisted machine learning with interactive, volume-subtending 3D cursor, which is incorporated by reference.

In some embodiments, the inputted medical data comprises terminology derived from patient history. In some embodiments, the inputted medical data comprises terminology derived from physical examination findings. In some embodiments, the inputted medical data comprises images derived from physical examination findings. In some embodiments, the inputted medical data comprises laboratory data. In some embodiments, the inputted medical data comprises terminology derived from radiological examinations. In some embodiments, the inputted medical data comprises images derived from radiological examinations.

In accordance with an aspect a method comprises a computer process comprising: generating a normal image database matched to a specific patient (e.g., age-matched, gender-matched, etc.); generating a pathological database (e.g., rib fracture, pneumonia, tumor, etc.); generating a surgical hardware database (e.g., hip arthroplasty hardware) as described in U.S. patent application Ser. No. 16/010,925, which is incorporated by reference; and, replacing features of the normal patient specific image with features of the pathological database (e.g., replacing normal rib with a fractured rib, replacing normal lung with pneumonia, etc.) and surgical hardware (e.g., hip replacement, etc.) as necessary.

In some embodiments, the computer-generated patient specific image comprises a 2D cartoon type illustration. In some embodiments, the computer-generated patient specific image comprises a 3D illustration. In some embodiments, the computer-generated patient specific image can be printed via a 3D printer. In some embodiments, the computer-generated patient specific image comprises a 3D interactive-type illustration. In some embodiments, the computer-generated patient specific image contains multiple pathologies (e.g., rib fracture and pneumonia). In some embodiments, the computer-generated patient specific image is provided to the patient via electronic means (e.g., email, website login, etc.). In some embodiments, the computer-generated patient specific image is provided to the patient via paper copy means (e.g., hand-out at the end of a physician's appointment, etc.). In some embodiments, the computer-generated patient specific image can be edited through user-input. In some embodiments, the computer-generated patient specific image is generated in a style optimized for health care providers for communication purposes. In some embodiments, the computer-generated patient specific image is generated in a style optimized for patients for educational purposes. In some embodiments, the computer-generated patient specific image has hyperlinks to prescribed treatment. Such hyperlinks can take the form of QR codes. In some embodiments, the computer-generated patient specific image has hyperlinks to expected clinical course. In some embodiments, the expected clinical course has computer-generated patient specific images over multiple time points. In some embodiments, the computer-generated patient specific image has hyperlinks to follow-up guidelines.

In some embodiment, a user selects an item, the item can be hyperlinked to the section of the report from where the image was generated. For example, the user clicks on the pathology image and the pathology report opens and the section of the pathology report that corresponds to the slide is highlighted.

Note that in some embodiments, any doctor can add to the patient specific image and the overall composite patient specific image can be stored and reviewed. In other embodiments, the patient specific image can be kept private by a single practitioner. Or the single practitioner could lock the patient specific image so that it is not editable. In some embodiments, there is a service specific patient specific image (e.g., patient specific image only for trauma surgeons, patient specific image only for radiologists, etc.).

In some embodiments, the patient specific image could be filled with a large number of findings. Therefore, a set of viewing options can be utilized. For example, the items could be filtered by priority level. For example, all findings could be shown. Only life threatening findings could be shown. Only findings related to cancer could be shown. Filtering options could be related to options including, but not limited to: anatomic feature (e.g., arm only); pathology category (e.g., cancer, trauma, infection, etc.); dangerous level (e.g., >50% chance of mortality); chronicity (e.g., acute within the last one week); and, pain level (e.g., findings that are associated with pain of a certain severity). In some embodiments, the filtered elements can be added back into the composite image.

In some embodiments, the image of a patient can be tracked over time (e.g., over multiple appointments or over multiple years) to see how problems have developed and resolved. In some embodiments, a movie can be generated showing this over time so a person's diagnoses and treatments can be understood efficiently.

In some embodiments, the computer generated patient specific image comprises a 3D dataset. In some embodiments, portions of the 3D dataset can be selected using a 3D volume cursor. Please see U.S. Pat. No. 9,980,691 for details on how to build and use the 3D cursor.

Some embodiments comprise an apparatus comprising: a processor; a display; a non-transitory memory having computer-executable instructions stored thereupon which, when executed by the processor of the head display unit, cause the apparatus to: input medical data; perform computer processing; generate a computer-generated patient specific image; and cause the computer-generated patient specific image to appear the display.

Some embodiments comprise a non-transitory computer readable medium having computer readable code thereon for generating a computer-generated patient specific image comprising: instructions for inputting medical data; instructions for performing computer processing; and instructions for generating a computer-generated patient specific image.

In some embodiments, this technique can be applied outside of the medical field in other industries.

BRIEF DESCRIPTION OF THE FIGURES

FIG. 4 illustrates the inputting of medical data comprises terminology derived from patient physical examination.

FIG. 5 illustrates the inputting of medical data comprises a photograph from the patient's physical examination.

FIG. 6 illustrates the inputting of medical data comprises data derived from laboratory/pathology data.

FIG. 7 illustrates the inputting of medical data comprises terminology derived from a radiology report.

FIG. 9A illustrates the composite image with multiple patient specific findings.

FIG. 9B illustrates a filtered image with two patient specific findings.

FIG. 9C illustrates a filtered image with a single patient specific findings.

FIG. 12A illustrates the patient specific image consisting of a 3D cartoon with a front view shown.

FIG. 12B illustrates the patient specific image consisting of a 3D cartoon with a side view shown.

FIG. 12C illustrates the patient specific image consisting of a 3D cartoon with a top view shown.

FIG. 13A illustrates the patient specific image which has been printed via a 3D printer, which in this example is a compression fracture of the T11 vertebrae.

FIG. 13B illustrates the patient specific image which has been printed via a 3D printer, which in this example is a normal T12 vertebrae.

FIG. 14A illustrates the patient specific image consisting of an interactive 3D cartoon illustrating the skin surface.

FIG. 14B illustrates the patient specific image consisting of an interactive 3D cartoon illustrating the bones.

FIG. 16A illustrates the computer generated patient specific image being displayed on a computer monitor.

FIG. 16B illustrates the computer generated patient specific image being displayed on a paper report.

FIG. 16C illustrates the computer generated patient specific image being displayed on an extended reality head display unit.

FIG. 20A illustrates the computer-generated patient specific image showing the computer generated patient specific image at day 1 of treatment.

FIG. 20B illustrates the computer-generated patient specific image showing the computer generated patient specific image at day 3 of treatment.

FIG. 20C illustrates the computer-generated patient specific image showing the computer generated patient specific image at day 5 of treatment.

DETAILED DESCRIPTIONS

Figure 1:
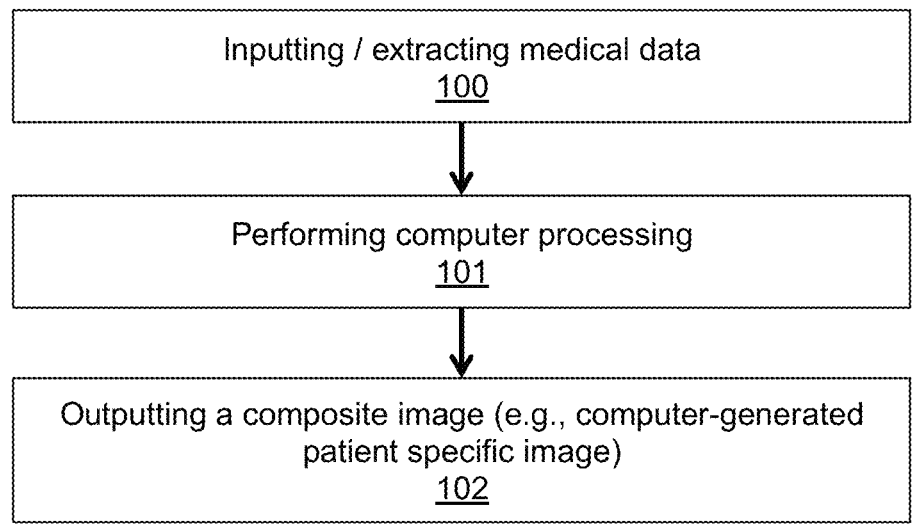
FIG. 1 illustrates the flow diagram showing the method of creating a computer-generated patient specific image comprising the inputting of medical data, performing computer processing and outputting a computer-generated patient specific image.

FIG. 1 illustrates the the flow diagram showing the method of creating a computer-generated patient specific image comprising the inputting of medical data, performing computer processing and outputting a computer-generated patient specific image. 100 illustrates a processing block comprising inputting/extracting medical data. 101 illustrates a processing block comprising performing computer processing. 102 illustrates a processing block comprising outputting a composite image (e.g., computer-generated patient specific image).

Figure 2:
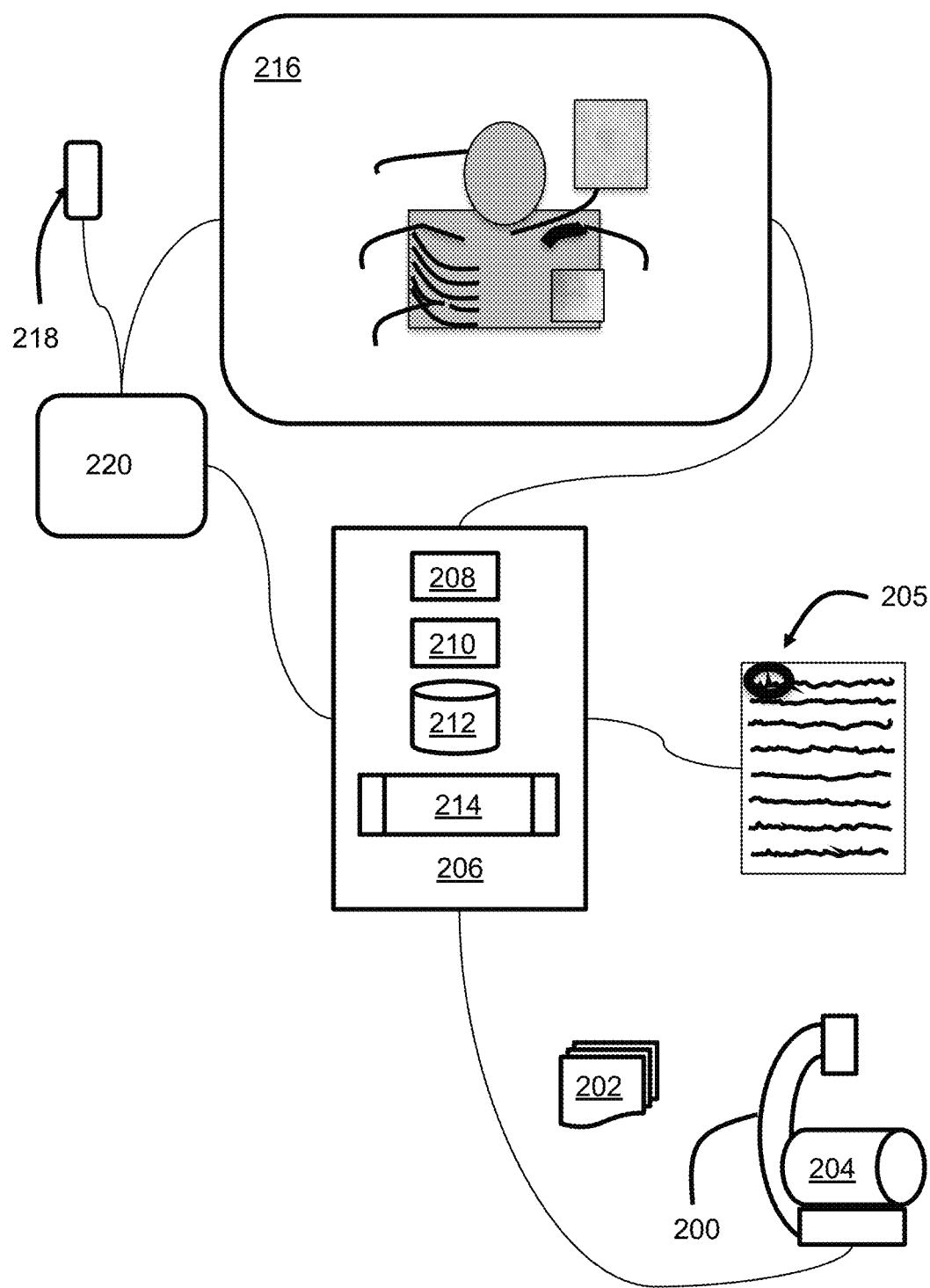
FIG. 2 illustrates an apparatus for implementing the process illustrated in FIG. 1.

FIG. 2 illustrates an apparatus for implementing the process illustrated in FIG. 1. A radiologic imaging system 200 (e.g., X-ray, ultrasound, CT (computed Tomography), PET (Positron Emission Tomography), or MRI (Magnetic Resonance Imaging)) is used to generate 2D medical images 202 of an anatomic structure 204 of interest. The 2D medical images 202 are provided to a processor 206, that includes processors 208 (e.g., CPUs and GPUs), volatile memory 210 (e.g., RAM), and non-volatile storage 212 (e.g. HDDs and SSDs). In addition, data 205 from other medical records (e.g., electronic medical record) is also inputted into the processor 206. A program 214 running on the image processor implements one or more of the steps described in FIG. 1. The computer generated patient specific image is displayed on an IO device 216. The IO device 216 may include a virtual reality headset, mixed reality headset, augmented reality headset, monitor, tablet computer, PDA (personal digital assistant), mobile phone, or any of a wide variety of devices, either alone or in combination. The IO device 216 may include a touchscreen, and may accept input from external devices (represented by 218) such as a keyboard, mouse, and any of a wide variety of equipment for receiving various inputs. However, some or all the inputs could be automated, e.g. by the program 214. Finally, as discussed further in FIG. 3 and the rest of this patent, a description of example features of the computer generated patient-specific image 220 are implemented, which facilitate viewing of medical images by medical personnel.

Figure 3:
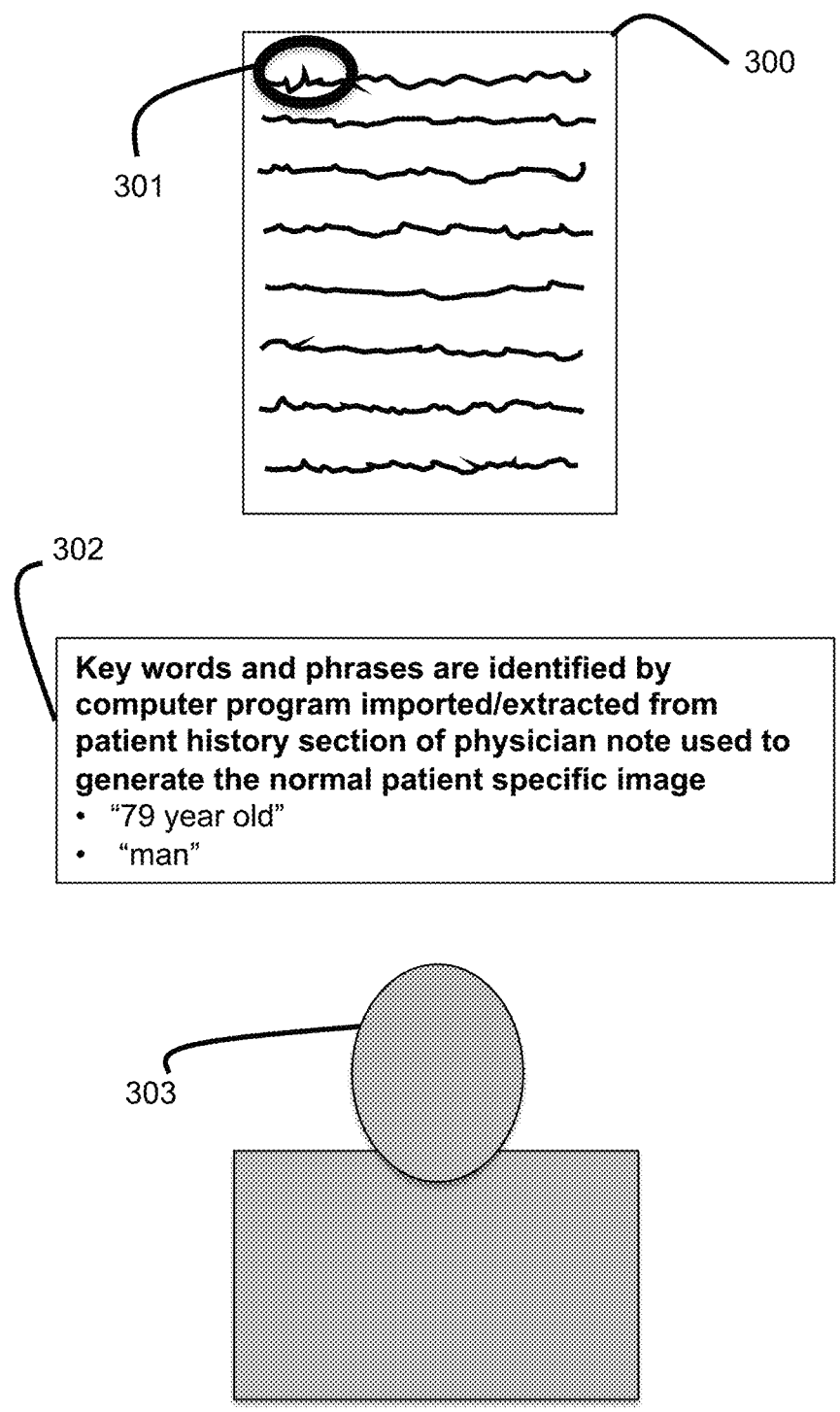
FIG. 3 illustrates a computer generated patient specific image based on inputted terminology derived from patient metadata.

FIG. 3 illustrates a computer generated patient specific image based on inputted terminology derived from patient metadata. Data 300 from medical records (e.g., electronic medical record) is illustrated. Certain key words or phrases 301 from the data 300 are identified. In this example, the words "79 year old" and "man" are identified" as illustrated in the text box 302. The patient specific image 303 is illustrated.

FIG. 4 illustrates the inputting of medical data comprises terminology derived from patient physical examination. Data 300 from medical records (e.g., electronic medical record) is illustrated. Certain key words or phrases 301 from the data 300 are identified (e.g., the words "79 year old" and "man"). Additional words 400 are identified from elsewhere in the electronic medical record including the words "left mid clavicle fracture deformity", which is illustrated in the text box 401. The patient specific image 303 is illustrated. The patient specific image 303 is modified with a normal right clavicle 402 (as illustrated by the thin, straight line) and a fractured left clavicle 403 (as illustrated by the curved thick line). Thus, in an instant, the patient specific image can communicate the findings. This saves time because at a glance at the image, the abnormality of the left clavicle fracture deformity 403 can be recognized.

FIG. 5 illustrates the inputting of medical data comprises a photograph from the patient's physical examination. Data 300 from medical records (e.g., electronic medical record) is illustrated. Certain key words or phrases 301 from the data 300 are identified (e.g., the words "79 year old" and "man"). Additional words 400 are identified from elsewhere in the electronic medical record data 300 including the words "left mid clavicle fracture deformity". Additional words 500 describing a healing cut on the left arm are also identified 500 and there is an associated photograph 501 taken by the physician of this site for documentation. Note that the photograph can be linked (e.g., through hyperlink to photo file) to the words in the physical examination. Note that a text box 502 states "Key words from physical examination section of physician note and associated photograph taken by physician during physical examination is imported/extracted by computer program and used to replace normal feature with an abnormal feature to generate a patient specific image including normal and/or abnormal findings: There is a healing cut on the left arm healing, see photograph." The patient specific image 303 is illustrated. The patient specific image 303 is modified with a normal right clavicle 402 (as illustrated by the thin, straight line) and a fractured left clavicle 403 (as illustrated by the curved thick line). The photograph of the healing cut on the left arm 503 is illustrated on the computer generated patient specific image 303. Thus, in an instant, the patient specific image can communicate the findings. This saves time because at a glance at the image, the abnormality of the left clavicle fracture deformity 403 and the healing cut on the left arm 503 can be recognized.

FIG. 6 illustrates the inputting of medical data comprises data derived from laboratory/pathology data. Data 300 from medical records (e.g., electronic medical record) is illustrated. Certain key words or phrases 301 from the data 300 are identified (e.g., the words "79 year old" and "man"). Additional words 400 are identified from elsewhere in the electronic medical record data 300 including the words "left mid clavicle fracture deformity". Additional words 500 describing a healing cut on the left arm are also identified 500 and there is an associated photograph taken by the physician of this site for documentation. Note that the photograph can be linked (e.g., through hyperlink to photo file) to the words in the physical examination. Additionally, words from a pathology section of the medical data are identified as illustrated by 600. In addition, the information from the pathology data 600 is linked (e.g., hyperlink) to a image from a pathology slide 601. Note that a text box 602 states "Data from laboratory/pathology pathology slide image from recent biopsy is imported/extracted by computer program and used to generate a patient specific image including normal and/or abnormal findings: Thyroid biopsy shows benign findings as shown in pathology slide." The patient specific image 303 is illustrated. The patient specific image 303 is modified with a normal right clavicle 402 (as illustrated by the thin, straight line) and a fractured left clavicle 403 (as illustrated by the curved thick line). The photograph of the healing cut on the left arm 503 is illustrated on the computer generated patient specific image 303. In addition, the image from the pathology slide 603 is also illustrated. Thus, in an instant, the patient specific image can communicate the findings. This saves time because at a glance at the image, the abnormality of the left clavicle fracture deformity 403 and the healing cut on the left arm 503 can be recognized.

FIG. 7 illustrates the inputting of medical data comprises terminology derived from a radiology report. Data 300 from medical records (e.g., electronic medical record) is illustrated. Certain key words or phrases 301 from the data 300 are identified (e.g., the words "79 year old" and "man"). Additional words 400 are identified from elsewhere in the electronic medical record data 300 including the words "left mid clavicle fracture deformity". Additional words 500 describing a healing cut on the left arm are also identified 500 and there is an associated photograph taken by the physician of this site for documentation. Note that the photograph can be linked (e.g., through hyperlink to photo file) to the words in the physical examination. Additionally, words from a pathology section of the medical data are identified as illustrated by 600 describing a thyroid biopsy. Additional terminology from the radiology report 700 is imported into the patient specific image. Note that a text box 701 states "Terminology from radiology report is imported/extracted by computer program and used to generate a patient specific image including normal and/or abnormal findings: Right anterior $6^{th}$ rib fracture". The patient specific image 303 is illustrated. The patient specific image 303 is modified with a normal right clavicle 402 (as illustrated by the thin, straight line) and a fractured left clavicle 403 (as illustrated by the curved thick line). The photograph of the healing cut on the left arm 503 is illustrated on the computer generated patient specific image 303. In addition, the image from the pathology slide 603 is also illustrated. 702 illustrates the right sided rib fracture is shown in the context of adjacent normal ribs. Thus, in an instant, the patient specific image can communicate the findings. This saves time because at a glance at the image, the abnormality of the rib fracture can instantly be visualized.

Figure 8:
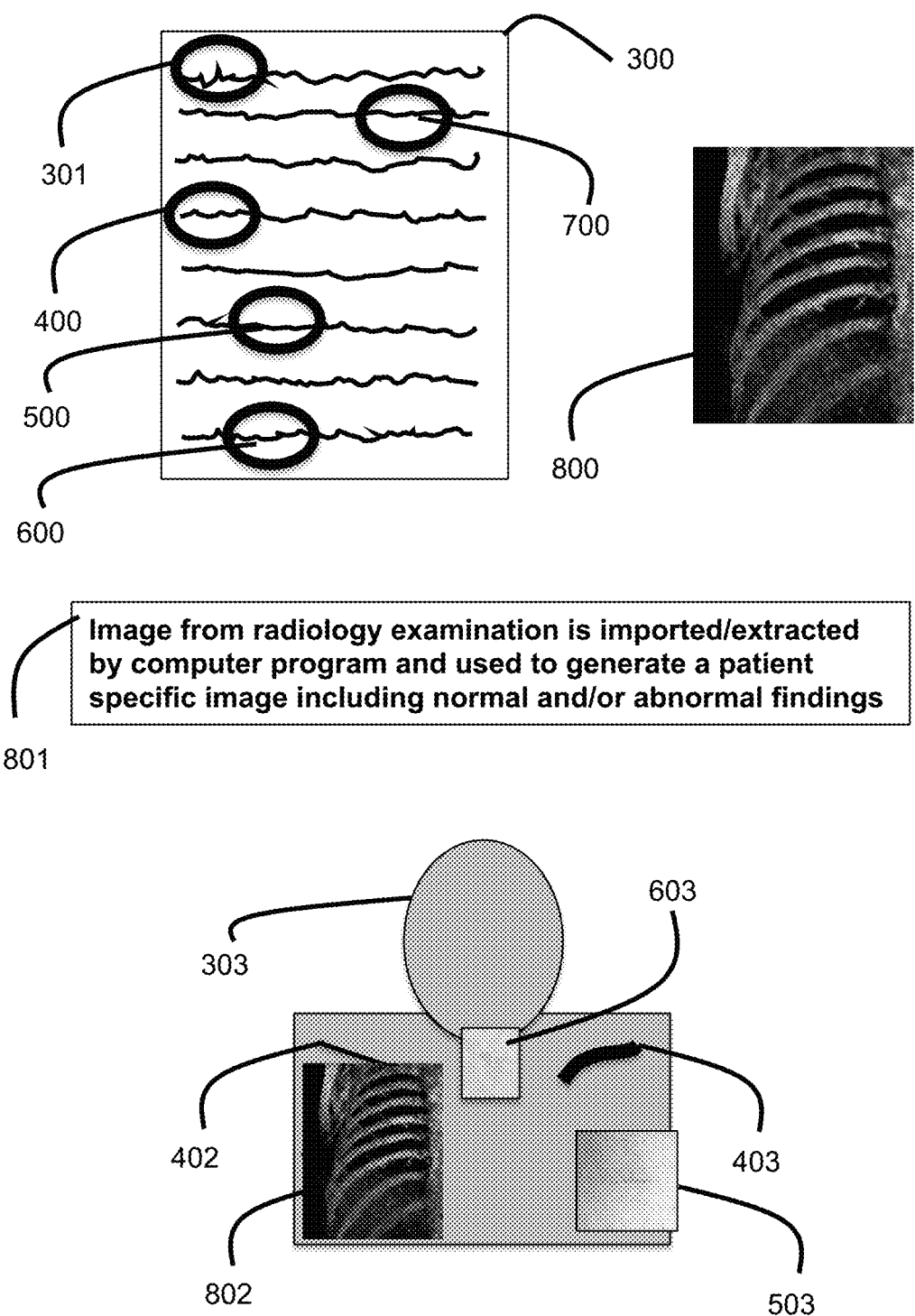
FIG. 8 illustrates the inputting of medical data comprising images from a radiology report.

FIG. 8 illustrates the inputting of medical data comprising images from a radiology report. Data 300 from medical records (e.g., electronic medical record) is illustrated. Certain key words or phrases 301 from the data 300 are identified (e.g., the words "79 year old" and "man"). Additional words 400 are identified from elsewhere in the electronic medical record data 300 including the words "left mid clavicle fracture deformity". Additional words 500 describing a healing cut on the left arm are also identified 500 and there is an associated photograph taken by the physician of this site for documentation. Note that the photograph can be linked (e.g., through hyperlink to photo file) to the words in the physical examination. Additionally, words from a pathology section of the medical data are identified as illustrated by 600 describing a thyroid biopsy. Additional terminology 700 from the radiology report is imported into the patient specific image. 800 illustrates a radiological image, which corresponds to the terminology 700 from the radiology report. Note that a text box 801 states "Image from radiology examination is imported/extracted by computer program and used to generate a patient specific image including normal and/or abnormal findings". The patient specific image 303 is illustrated. The patient specific image 303 is modified with a normal right clavicle 402 (as illustrated by the thin, straight line) and a fractured left clavicle 403 (as illustrated by the curved thick line). The photograph of the healing cut on the left arm 503 is illustrated on the computer generated patient specific image 303. In addition, the image from the pathology slide 603 is also illustrated. 802 illustrates a radiological image, which corresponds to the terminology 700 from the radiology report. Thus, in an instant, the patient specific image can communicate the findings. This saves time because at a glance at the image, the abnormality of the rib fracture can instantly be visualized.

FIG. 9A illustrates the composite image with multiple patient specific findings. The patient specific image 303 illustrates a normal right clavicle 402 (as illustrated by the thin, straight line) and an old, chronic fractured left clavicle 403 (as illustrated by the curved thick line). The photograph of the healing cut on the left arm 503 is illustrated on the computer generated patient specific image 303. In addition, the image from the pathology slide 603 is also illustrated. 702 illustrates an acute right sided rib fracture is shown in the context of adjacent normal ribs. Thus, in an instant, the patient specific image can communicate the findings. Generally, this saves time because at a glance at the image, the abnormality of the rib fracture can instantly be visualized. However, there are some cases wherein a user may only be interested in certain kinds of pathology. For example, a trauma surgeon may only be interested in traumatic injuries. In this case, filtering can be applied to eliminate aspects of the patient specific image that are of non-interest. A drop down menu is the preferred embodiment to accomplish this.

FIG. 8B illustrates a filtered image with two patient specific findings. In this event, the trauma surgeon is only interested in the traumatic injuries the patient has sustained. The patient specific image 303 illustrates an old, chronic fractured left clavicle 403 (as illustrated by the curved thick line). 702 illustrates the acute right sided rib fracture is shown. Thus, the trauma surgeon can filter the image from FIG. 9A and yield the image in FIG. 9B, so the trauma surgeon is not bogged down with findings that are not relevant. Note that in some embodiments, any doctor can add to the patient specific image and the overall composite patient specific image can be stored and reviewed. In other embodiments, the patient specific image can be kept private by a single practitioner. Or the single practitioner could lock the patient specific image so that it is not editable.

FIG. 9C illustrates a filtered image with a single patient specific findings. In this event, the trauma surgeon is only interested in the acute subset of the traumatic injuries the patient has sustained. The patient specific image 303 illustrates the acute right sided rib fracture 702. Note that this greatly simplifies the ability to review. Instantly, the trauma surgeon can see that there is only one acute finding and this is much quicker to interpret as compared to FIG. 9A.

Figure 10:
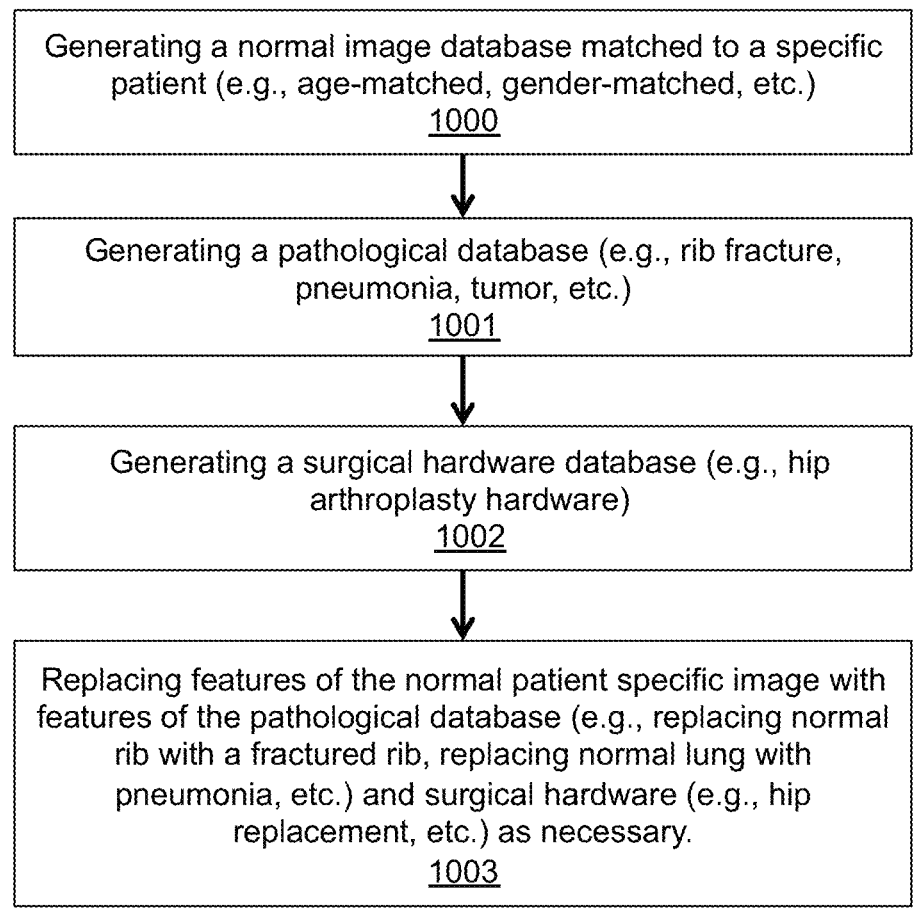
FIG. 10 illustrates the flow diagram showing the method of computer processing to generate a patient specific image.

FIG. 10 illustrates the the flow diagram showing the method of computer processing to generate a patient specific image. Step 1000 illustrates generating a normal image database matched to a specific patient (e.g., age-matched, gender-matched, etc.). Step 1001 illustrates generating a pathological database (e.g., rib fracture, pneumonia, tumor, etc.). Step 1002 illustrates generating a surgical hardware database (e.g., hip arthroplasty hardware). Step 1003 illustrates replacing features of the normal patient specific image with features of the pathological database (e.g., replacing normal rib with a fractured rib, replacing normal lung with pneumonia, etc.) and surgical hardware (e.g., hip replacement, etc.) as indicated by the computer program.

Figure 11:
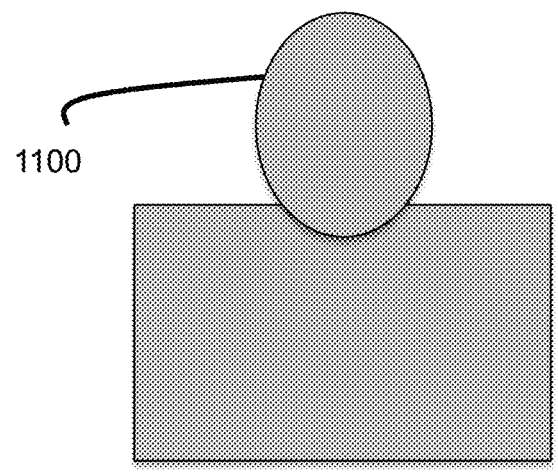
FIG. 11 illustrates the patient specific image consisting of a 2D cartoon.

FIG. 11 illustrates the patient specific image consisting of a 2D cartoon. 1100 illustrates the 2D cartoon.

FIG. 12A illustrates the patient specific image consisting of a 3D cartoon with a front view shown.

FIG. 12B illustrates the patient specific image consisting of a 3D cartoon with a side view shown.

FIG. 12C illustrates the patient specific image consisting of a 3D cartoon with a top view shown. Note that the 3D cartoon comprises a 3D dataset, so can be viewed in a flat 2D monitor as a volume rendered image or on an extended reality head display unit.

FIG. 13A illustrates the patient specific image which has been printed via a 3D printer, which in this example is a compression fracture of the T11 vertebrae.

FIG. 13B illustrates the patient specific image which has been printed via a 3D printer, which in this example is a normal T12 vertebrae.

FIG. 14A illustrates the patient specific image consisting of an interactive 3D cartoon illustrating the skin surface.

FIG. 14B illustrates the patient specific image consisting of an interactive 3D cartoon illustrating the bones. Note that the 3D cartoon is interactive. For example, the user can interactively choose to display the bones or the skin surface, etc. The 3D cartoon is a virtual object so can be viewed in methods disclosed by U.S. Pat. No. 8,384,771 or methods disclosed in U.S. patent application Ser. No. 16/524,275.

Figure 15:
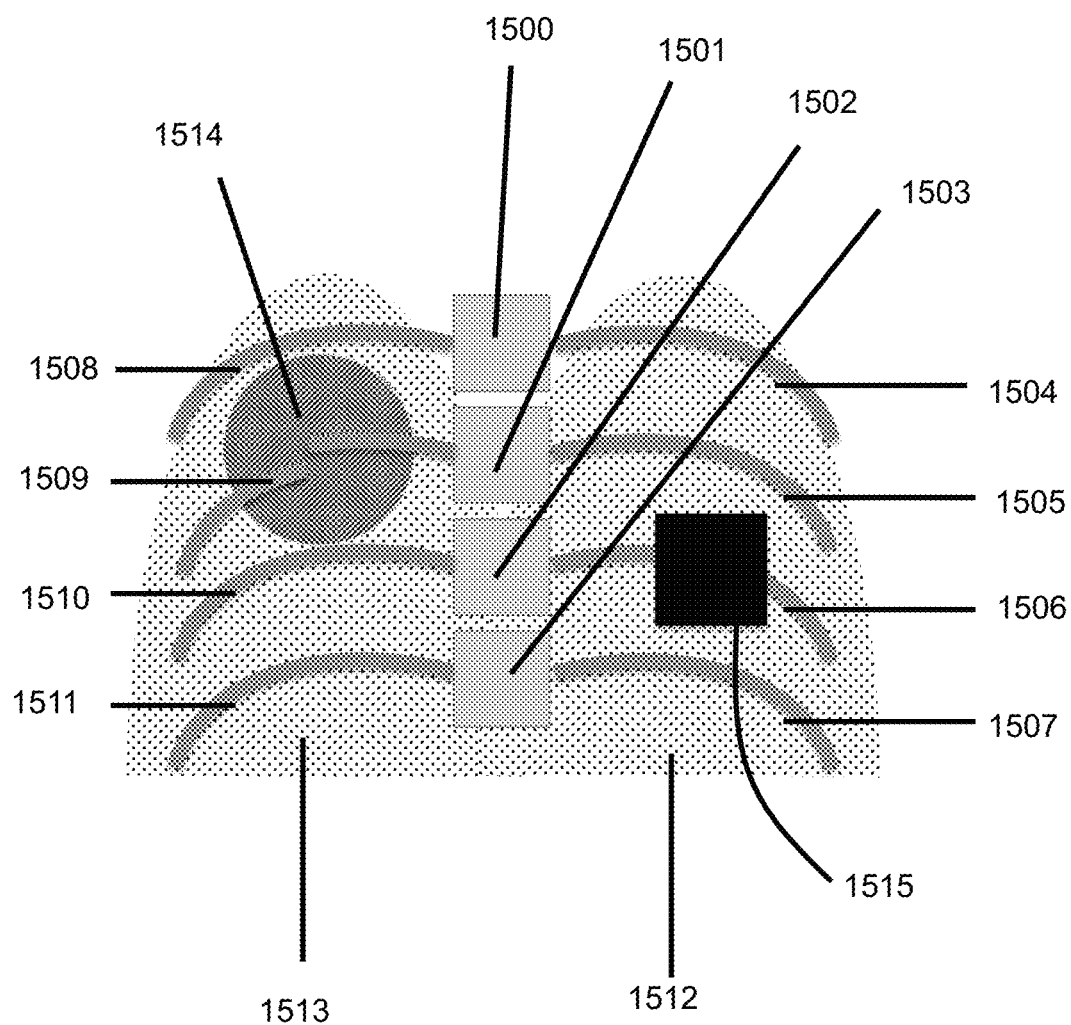
FIG. 15 illustrates an example of a 3D patient specific image consisting of multiple pathologies including pneumonia and a rib fracture as well as a left-sided pacemaker.

FIG. 15 illustrates an example of a 3D patient specific image consisting of multiple pathologies including pneumonia and a rib fracture. 1500 illustrates the T1 vertebrae. 1501 illustrates the T2 vertebrae. 1502 illustrates the T3 vertebrae. 1503 illustrates the T4 vertebrae. 1504 illustrates the left first rib, which is normal. 1505 illustrates the left second rib, which is normal. 1506 illustrates the left third rib, which is normal. 1507 illustrates the left fourth rib, which is normal. 1508 illustrates the right first rib, which is normal. 1509 illustrates the right second rib, which is fractured. 1510 illustrates the right third rib, which is normal. 1511 illustrates the right fourth rib, which is normal. 1512 illustrates the left lung, which is normal. 1513 illustrates the right lung with an area of pneumonia 1514. A left sided pacemaker 1515 is also shown. To best communicate the areas of abnormality to the patient, they can be shown in false color or blinking or other visual representation adjustment logic so that they are easily noticed by the user.

FIG. 16A illustrates the computer generated patient specific image being displayed on a computer monitor.

FIG. 16B illustrates the computer generated patient specific image being displayed on a paper report.

FIG. 16C illustrates the computer generated patient specific image being displayed on an extended reality head display unit.

Figure 17A:
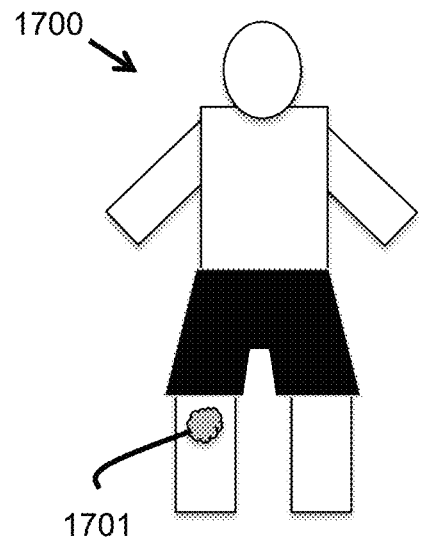
FIG. 17A illustrates the computer-generated patient specific image.

FIG. 17A illustrates the computer-generated patient specific image. 1700 illustrates a computer-generated patient specific image. 1701 illustrates a skin lesion over the right leg.

Figure 17B:
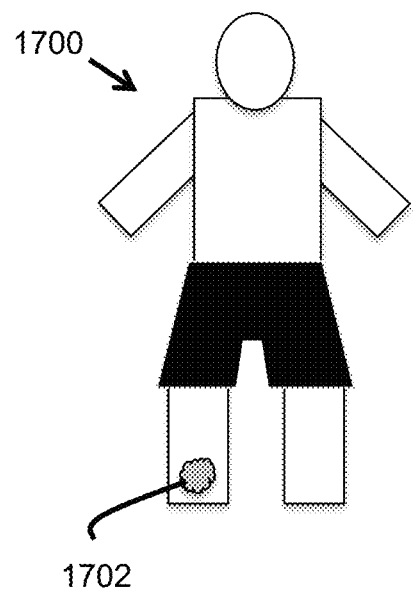
FIG. 17B illustrates the computer-generated patient specific image, which has been edited by a physician.

FIG. 17B illustrates the computer-generated patient specific image, which has been edited by a physician. 1700 illustrates a computer-generated patient specific image. 1702 illustrates a skin lesion over the right leg, which has been moved to a more inferior position on the leg. Note that a click and drag type maneuver can be performed by the provider to edit the computer-generated patient specific image so that it more accurately represents the patient.

Figure 18A:
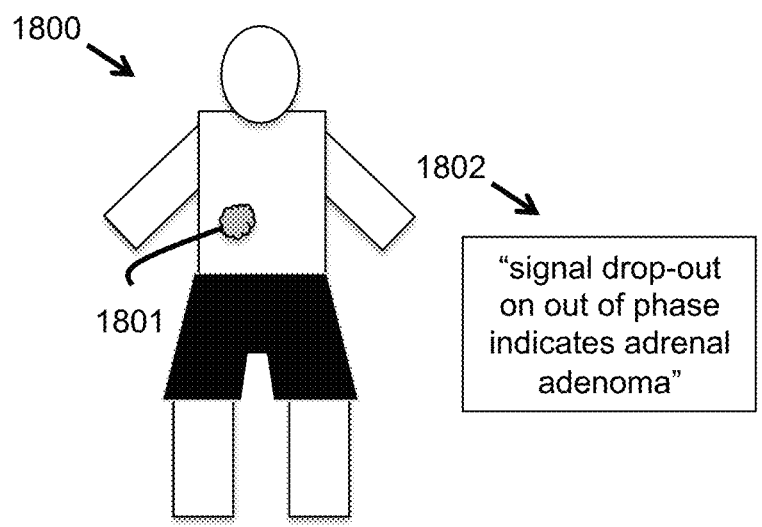
FIG. 18A illustrates the patient specific image optimized for physician to physician communication.

FIG. 18A illustrates the patient specific image optimized for physician to physician communication. 1800 illustrates the computer generated patient specific image. 1801 illustrates the adrenal adenoma. 1802 illustrates a sign post illustrating language optimized for communication from physician to physician, which states "signal drop-out on out of phase indicates adrenal adenoma".

Figure 18B:
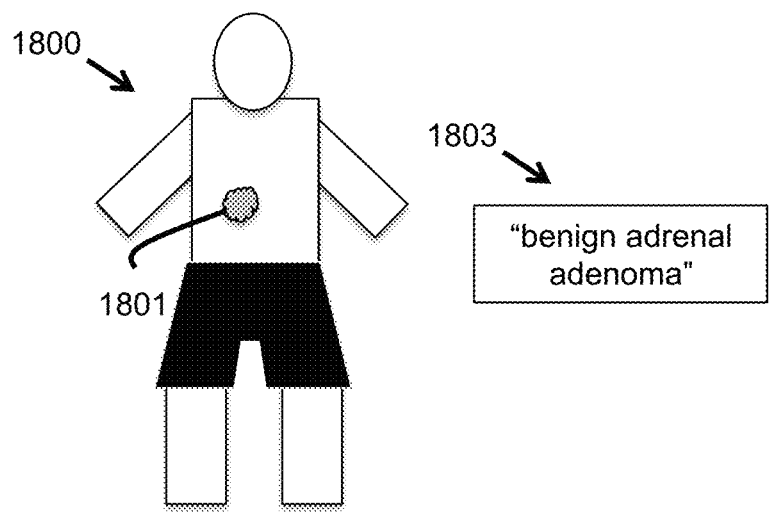
FIG. 18B illustrates the patient specific image optimized for physician to physician communication.

FIG. 18B illustrates the patient specific image optimized for physician to physician communication. 1800 illustrates the computer generated patient specific image. 1801 illustrates the adrenal adenoma. 1802 illustrates a sign post illustrating language optimized for communication from physician to patient, which states "benign adrenal adenoma".

Figure 19:
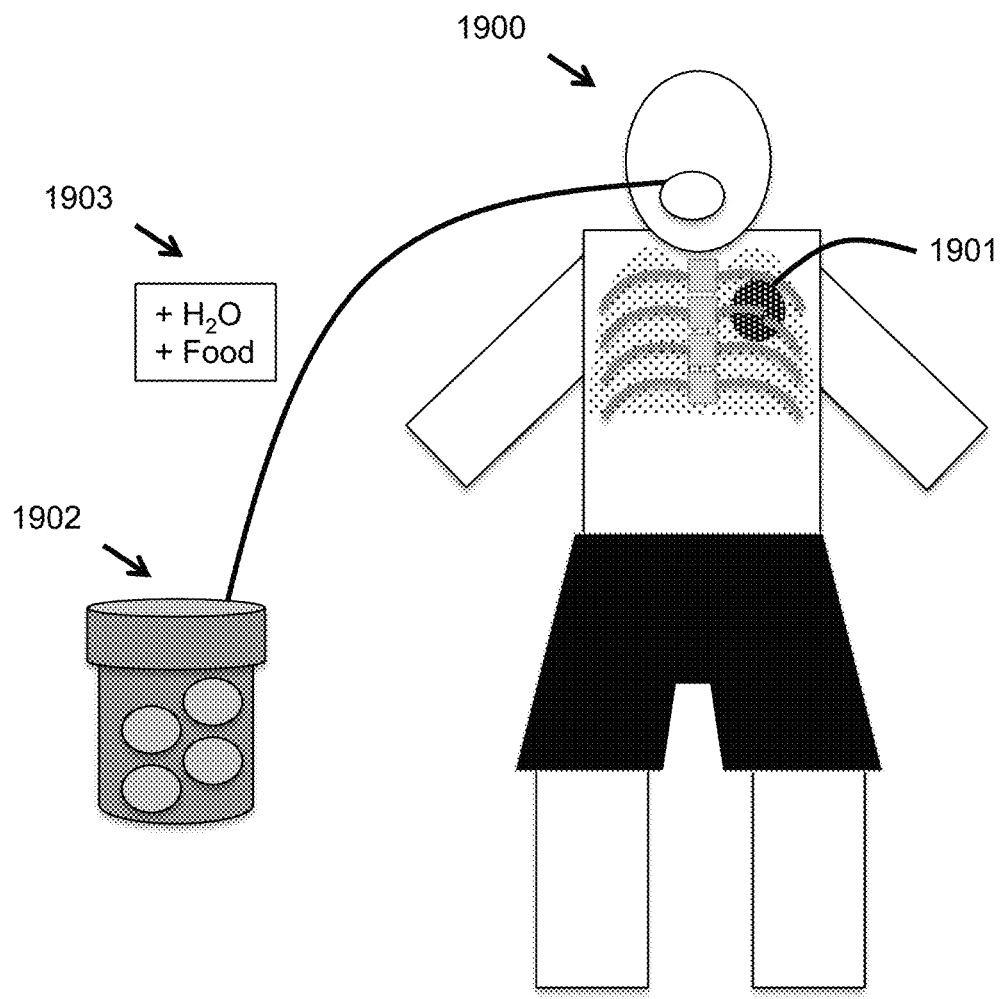
FIG. 19 illustrates a computer-generated patient specific image illustrating the prescribing of a medication to be taken by mouth.

FIG. 19 illustrates a computer-generated patient specific image illustrating the prescribing of a medication to be taken by mouth. 1900 illustrates the computer-generated patient specific image. 1901 illustrates the left lung pneumonia. 1902 illustrates the bottle of pills. 1903 illustrates a sign post with "+H2O" and "+Food" indicating instructions for the patient.

FIG. 20A illustrates the computer-generated patient specific image showing the computer generated patient specific image at day 1 of treatment. 2000 illustrates a sign post stating "day 1". 2001 illustrates a sign post stating "+H2O" and "+Food". 2002 illustrates a computer-generated patient specific image illustrating the left lung pneumonia 2003. 2004 illustrates a bottle of pills, which communicates to the patient that the treatment for the pneumonia is the medication. 2005 illustrates a sign post, which states "Take once daily: 4 pills remaining after you take your dose". 2006 illustrates a sign post, which states "pneumonia".

FIG. 20B illustrates the computer-generated patient specific image showing the computer generated patient specific image at day 3 of treatment. 2007 illustrates a sign post stating "day 3". 2008 illustrates a sign post stating "+H2O" and "+Food". 2009 illustrates a computer-generated patient specific image illustrating the left lung pneumonia 2010, which is improving. 2011 illustrates a bottle of pills, which communicates to the patient that the treatment for the pneumonia is the medication. 2012 illustrates a sign post, which states "Take once daily: 2 pills remaining after you take your dose". 2013 illustrates a sign post, which states "pneumonia is expected to be improving".

FIG. 20C illustrates the computer-generated patient specific image showing the computer generated patient specific image at day 5 of treatment. 2014 illustrates a sign post stating "day 5". 2015 illustrates a sign post stating "+H2O" and "+Food". 2016 illustrates a computer-generated patient specific image illustrating the left lung pneumonia 2017. 2018 illustrates a bottle of pills, which communicates to the patient that the treatment for the pneumonia is the medication. 2019 illustrates a sign post, which states "Take once daily: 0 pills remaining after you take your dose". 2020 illustrates a sign post, which states "pneumonia is expected to be completely resolved". Thus, FIGS. 20A, 20B, and 20C together explain the expected clinical course with taking the medication as prescribed.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method of creating a computer-generated patient specific image comprising:
   inputting of medical data from a patient
      wherein said medical data comprises terminology,
      wherein said medical data does not comprise a medical image,
      wherein said terminology is derived from at least one physician report,
      wherein a first set of said terminology corresponds to anatomic features, and
      wherein a second set of said terminology corresponds to pathologic features;
   performing computer processing to generate said computer-generated patient specific image
      wherein said computer processing uses said first set of said terminology from said at least one physician report to generate at least one anatomic cartoon feature,
      wherein said computer processing uses said second set of said terminology from said at least one physician report to generate at least one pathologic cartoon feature; and
   displaying said computer-generated patient specific image
      wherein said computer-generated patient specific image comprises said at least one anatomic cartoon feature and said at least one pathologic cartoon feature.

2. The method of claim 1 wherein the inputted medical data comprises at least one of the group consisting of: a cartoon diagram derived from terminology derived from patient history; a cartoon diagram derived from terminology derived from physical examination findings; photograph images derived from physical examination findings; a cartoon diagram derived from laboratory data; a cartoon diagram derived from terminology derived from radiological examinations; and, images derived from radiological examinations.

3. The method of claim 1 wherein the computer processing comprises generating an age-matched, gender matched cartoon for a specific patient and a cartoon for a pathology for the specific patient.

4. The method of claim 1 wherein the computer-generated patient specific image comprises at least one of the group of a 2D cartoon and a 3D cartoon.

5. The method of claim 4 wherein the 3D cartoon of claim 4 can be printed via a 3D printer.

6. The method of claim 1 wherein the computer-generated patient specific image is interactive wherein a different anatomic features of the cartoon are displayed upon user selection.

7. The method of claim 1 further comprising wherein the computer-generated patient specific image is comprised of at least two items wherein a first item is displayed and a second item is filtered.

8. The method of claim 1 wherein the computer-generated patient specific image comprises generating an age-matched, gender matched cartoon for the specific patient and cartoon for a surgical hardware for the specific patient.

9. The method of claim 1 wherein the computer-generated patient specific image is displayed via at least one of the group consisting of: displayed on a computer monitor; printed; and, displayed on a virtual reality or augmented reality 3D headset.

10. The method of claim 1 wherein the computer-generated patient specific image is provided to the patient via paper copy.

11. The method of claim 1 wherein the computer-generated patient specific image can be edited through user-input.

12. The method of claim 1 wherein the computer-generated patient specific image is generated in a style optimized for at least one of the group consisting of: health care providers for communication purposes; and, patients for educational purposes.

13. The method of claim 1 wherein at least one item within the computer-generated patient specific image has a hyperlink to a prescribed treatment.

14. The method of claim 1 wherein the computer-generated patient specific image has at least one hyperlink to an expected clinical course.

15. The method of claim 14 wherein the computer-generated patient specific images changes over multiple time points.

16. The method of claim 1 wherein the computer-generated patient specific image has at least one hyperlink to a follow-up guidelines.

17. The method of claim 1 wherein a patient's medical history over multiple visits can be illustrated through multiple sequentially displayed patient specific images.

18. The method of claim 1 wherein a patient's medical history pertaining to a specific organ system can be reviewed and displayed.

19. An apparatus comprising:
a processor;
a display; and
a non-transitory memory having computer-executable instructions stored thereupon which, when executed by the processor of the head display unit, cause the apparatus to:
input medical data from a patient
wherein said medical data comprises terminology,
wherein said medical data does not comprise a medical image,
wherein said terminology is derived from at least one physician report,
wherein a first set of said terminology corresponds to anatomic features, and
wherein a second set of said terminology corresponds to pathologic features;
perform computer processing to generate a computer-generated patient specific image
wherein said computer processing uses said first set of said terminology from said at least one physician report to generate at least one anatomic cartoon feature,
wherein said computer processing uses said second set of said terminology from said at least one physician report to generate at least one pathologic cartoon feature; and
present said computer-generated patient specific image on said display wherein said computer-generated patient specific image comprises said at least one anatomic cartoon feature and said at least one pathologic cartoon feature.

20. A non-transitory computer readable medium having computer readable code thereon for generating a computer-generated patient specific image comprising:
instructions for using medical data from a patient
wherein said medical data comprises terminology,
wherein said medical data does not comprise a medical image,
wherein said terminology is derived from at least one physician report,
wherein a first set of said terminology corresponds to anatomic features, and
wherein a second set of said terminology corresponds to pathologic features;
instructions for performing computer processing to generate a computer-generated patient specific image
wherein said computer processing uses said first set of said terminology from said at least one physician report to generate at least one anatomic cartoon feature,
wherein said computer processing uses said second set of said terminology from said at least one physician report to generate at least one pathologic cartoon feature; and
instructions for generating said computer-generated patient specific image wherein said computer-generated patient specific image comprises said at least one anatomic cartoon feature and said at least one pathologic cartoon feature.

* * * * *